(12) United States Patent
Lardy et al.

(10) Patent No.: US 7,829,721 B2
(45) Date of Patent: Nov. 9, 2010

(54) SPECIFIC CASPASE-10 INHIBITORS

(75) Inventors: Claude Lardy, Lyons (FR); Marc Lecomte, Lissieu (FR); Catherine Vidal, Lyons (FR); Thierry Convard, Sathonay-Camp (FR); Stéphane Yvon, Goyrans (FR); Marie Noelle Denuault, Saint Germain sur-Sauthe (FR); Denis Descours, Villeurbanne (FR)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 11/791,922

(22) PCT Filed: Nov. 2, 2005

(86) PCT No.: PCT/EP2005/011686

§ 371 (c)(1),
(2), (4) Date: Jan. 22, 2008

(87) PCT Pub. No.: WO2006/058592

PCT Pub. Date: Jun. 8, 2006

(65) Prior Publication Data

US 2008/0255173 A1  Oct. 16, 2008

(30) Foreign Application Priority Data

Dec. 1, 2004 (FR) .................................. 04 12765

(51) Int. Cl.
*A61K 31/44* (2006.01)
*A61K 31/192* (2006.01)
*C07C 57/38* (2006.01)
*C07D 213/55* (2006.01)
*A61P 27/02* (2006.01)

(52) U.S. Cl. .................. 546/342; 514/277; 514/570; 562/492

(58) Field of Classification Search .................. None
See application file for complete search history.

(56) References Cited

U.S. PATENT DOCUMENTS 5,352,788 A   10/1994  Bernhart et al.
2004/0034064 A1  2/2004  Kuduk et al.

FOREIGN PATENT DOCUMENTS

| DE | 3026402 A1 | 2/1982 |
| JP | 56125339 | * 10/1981 |
| WO | WO 93/15717 A | 8/1993 |
| WO | WO 93/15732 A | 8/1993 |
| WO | WO 01/39792 A | 6/2001 |
| WO | WO 01/81312 A | 11/2001 |

OTHER PUBLICATIONS

Boye et al. Helv Chim Acta, 72: 1690-1696, 1989.*
English translation of JP-56125339 abstract.*
Boye O et al : << Natural Products. Antitubulin Effect of Congeners of N-Acetylcolchinyl Methyl Ether : Synthesis of Optically Active 5-Acetamidodeaminocolchinyl Methyl Ehter and of Demethoxy Analogues of Deaminocolchinyl Methyl Ether >> Canadian Journal of Chemistry, National Research Council, Ottowa, CA, vol. 70, No. 5, 1992, pp. 1237-1249, XP009047355 ISSN : 0008-4042 cited in the application compounds, 19, 36 p. 1245 ; compound 19 p. 1247; compound 36.

* cited by examiner

*Primary Examiner*—Brian-Yong S Kwon
*Assistant Examiner*—Bong-Sook Baek
(74) *Attorney, Agent, or Firm*—Millen, White, Zelano, Branigan, P.C.

(57) ABSTRACT

The invention relates to compounds of the general formula (I), and to their use as caspase-10 inhibitors, especially for the treatment of diabetic retinopathy.

4 Claims, 1 Drawing Sheet

SPECIFIC CASPASE-10 INHIBITORS

Diabetic retinopathy represents one of the most debilitating microvascular complications of diabetes, which can lead in its final stage to blindness (Grange, *La Rétinopathie diabétique* [Diabetic Retinopathy], Masson, Paris, Milan, Barcelona, 1995, p. 632; Frank, *Diabetic Retinopathy* (Chapter 1), in Progress in Retinal and Eye Research, vol. 14 No. 2), Elsevier Science Ltd (Great Britain), 1995, pp. 361-392; Aiello et al., *Diabetes Care*, 21, 1998, 227-293). It is the second cause of acquired blindness in our countries after age-related macular degeneration (Nathan et al., *Diabetes Care*, 14, 1991, 26-33), and the risk of a diabetic patient becoming blind is estimated at 25 times higher than that of the general population (Kahn et al., *Am. J. Opthalmol.* 78, 1974, 58-67). At the present time, there is no preventive or curative pharmacological treatment for this complication, the only treatment being retinal photocoagulation by laser or vitreotectomy in the more severe cases (Frank, *Diabetic Retinopathy* (Chapter 1), in Progress in Retinal and Eye Research, vol. 14 (No. 2), Elsevier Science Ltd (Great Britain), 1995, pp. 361-392; Aiello et al., *Diabetes Care*, 21, 1998, 227-293).

In its early phase, cellular alterations in the retinal capillaries (see FIG. 1) have been demonstrated, especially a selective disappearance of pericytes, altering the numerical ratio of the pericytes relative to the endothelial cells of the retinal capillaries, going from 1 to 1 in the normal situation to 0.3 to 1 in the pathological situation and even 0.1 for the final stages (Cogan et al., *Arch. Opthalmol.* 60, 1961, 100-112; Kuwabara et al., *Arch. Opthalmol.* 69, 1963, 492-502). During this phase, death of the pericytes by apoptosis has been detected (Mizutani et al., *J. Clin. Invest.* 97, 1996, 2883-2890; Li et al., *Chin. Med. J.* (Engl.) 110, 1997, 659-663; Podesta et al., *Am. J. Pathol.* 156, 2000, 1025-1032), but the intracellular signalling pathway(s) via which they disappear was (were) not known. The relationship between the reduction in the number of pericytes and the worsening of the clinical signs of retinopathy has recently been documented with the study of a model of mice that are transgenic for the gene for the growth factor PDGF-$\beta$. The mice whose gene is inactivated, PDGF-$\beta$-/-, have no pericytes and are non-viable; the heterozygous mice in which only one copy has been inactivated, PDGF-$\beta$+/-, are viable and have 30% fewer pericytes than the wild-type mice, PDGF-$\beta$+/+. The diabetic heterozygous mice PDGF-$\beta$ P+/-, which have fewer pericytes than the diabetic wild-type mice, progress twice as quickly in terms of microvascular impairments quantified by the acellular capillaries, suggesting a direct relationship between the loss of retinal pericytes and the progress of retinopathy (Hammes et al., *Diabetes* 51, 2002, 3107-3112).

Patent application FR 00/13640 (WO 02/34201 A2) describes the clarification of this chain of events leading to apoptosis of the pericytes induced by AGEs (Advanced Glycation End products). One series of targets—among which is caspase-10—have been identified, which allow a pharmacological intervention in order to prevent their disappearance, and the invention relates to the use of inhibitors of these targets, used alone or in combination, to eradicate the process of loss of the pericytes by apoptosis observed in the early phase of diabetic retinopathy. The use of such pharmacological inhibitors, such as those of caspase-10, should be beneficial for the treatment or prevention of diabetic retinopathy, by protecting the pericytes against apoptosis and thus slowing down its progress towards the final stages of this complication, which are the most serious.

The present invention relates to novel selective caspase-10 inhibitors of the formula (II), which are active at 5-25 $\mu$M, non-cytotoxic, and which inhibit the AGE-induced apoptosis of pericytes, for the treatment of or preventing diabetic retinopathy in its early stage.

Diabetic retinopathy is an evolutive diabetic complication, passing from a "basal" stage (background retinopathy) to a final phase known as "proliferative retinopathy", in which there is formation of new fragile retinal vessels, leading to severe haemorrhaging, occasionally with detachment of the retina, and to loss of vision (Grange, *La Rétinopathie diabétique* [Diabetic Retinopathy], Masson, Paris, Milan, Barcelona, 1995, p. 632; Frank, *Diabetic Retinopathy* (Chapter 1), in Progress in Retinal and Eye Research, vol. 14 (No. 2), Elsevier Science Ltd (Great Britain), 1995, pp. 361-392). In background retinopathy, the microvascular lesions are characterised by microaneurisms, small point haemorrhages, exudates and venous dilations (Palmberg, Diabetic Retinopathy, Diabetes 26, 1977, 703-709; ETDRS, *Early Treatment Diabetic Retinopathy Study Research Group*, Report No. 10, *Opthalmology* 98, 1991, 786-791). This background retinopathy may remain clinically silent for a long time. At this "background" stage, cellular and structural alterations of the retinal capillaries have been noted, from examination of the retinas of diabetic patients collected post-mortem and compared with retinas of normal individuals of comparable ages.

Figure 1:
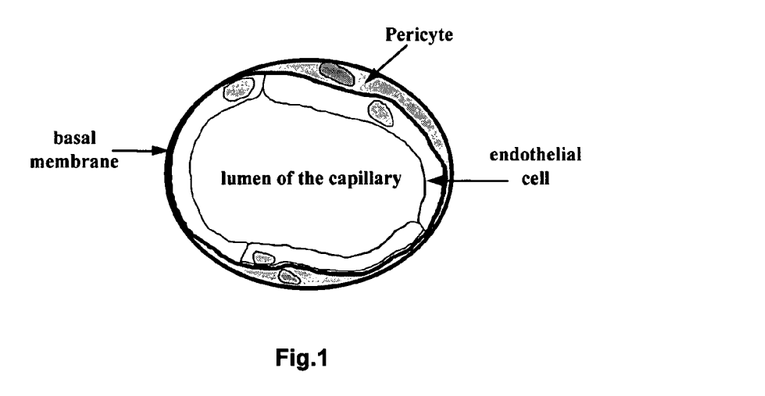
FIG. 1 illustrates a retinal capillary.

The retinal capillaries are lined with endothelial cells, on the luminal side of the vessel, and with pericytes (or wall cells) located on the exterior and buried in the basal membrane of the vessel. FIG. 1 illustrates a retinal capillary.

In the human retina or the rat retina, the numerical ratio of the pericytes to the endothelial cells is 1 to 1 (Kuwabara et al., *Arch. Opthalmol.* 69, 1963, 492-502). The impairments observed at this early stage consist of thickening of the basal membrane of the capillaries (Friedenwald, *Diabetic Retinopathy, Am. J. Opthalmol.* 33, 1950, 1187-1199) and selective disappearance of the pericytes (Cogan et al., *Arch. Opthalmol.* 60, 1961, 100-112; Kuwabara et al., *Arch. Ophthalmol.* 69, 1963, 492-502), leading to a ratio of the number of pericytes to endothelial cells of less than 1 to 1 (Kuwabara et al., *Arch. Opthalmol.* 69, 1963, 492-502). Recent studies performed using human retinas removed post-mortem from long-term diabetic patients have made it possible to show that the pericytes died by apoptosis, programmed cell death, rather than by necrosis, sudden death observed following a toxic attack (Mizutani et al., *J. Clin. Invest.* 97, 1996, 2883-2890; Li et al., *Chin. Med. J.* (Engl.) 110, 1997, 659-663; Podesta et al., *Am. J. Pathol.* 156, 2000, 1025-1032). Detection of the apoptotic pericytes was performed in situ, on the whole retinas by a technique of staining of the nuclei of the cells entering into apoptosis, the TUNEL method (Terminal Deoxynucleotidyl Transferase Mediated dUDP Nick-end Labeling) (Mizutani et al., *J. Clin. Invest.* 97, 1996, 2883-2890). Another recent study has also shown that anti-pericyte autoantibodies were detectable in type 2 diabetic patients and that they were associated with the early stages of diabetic retinopathy, suggesting an expression of novel antigens by the "active" pericytes during diabetes (Nayak et al., *Diabetologia* 46, 2003, 511-513).

The underlying cell mechanisms via which the pericytes die by apoptosis are still largely unknown. The studies undertaken in the past by The Diabetes Control Complications Trial Research Group (DCCT), *N. Engl. J. Med.* 239, 1993, 977-986) or the UK Prospective Diabetes Study Group (UKPDS), *Lancet* 352 (33, 1998a, 837-853 and 34, 1998b, 854-865) have shown the key role of the control of hyperglycaemia in the development of diabetic retinopathy. A possible mechanism via which glucose can lead to the death of the pericytes is the increased production and accumulation of advanced glycation end products or AGEs formed by non-enzymatic glycosylation—or glycation—of proteins, DNA or lipids (Maillard reaction) which have been demonstrated in many studies during diabetes (Thornalley, *Clin. Lab.* 45, 1999, 261-273). The amount of AGEs measured in the skin of diabetic patients is moreover strongly correlated with the severity of the vascular complications (Beisswenger et al., *Diabetes* 44, 1995, 824-829).

Figure 2:
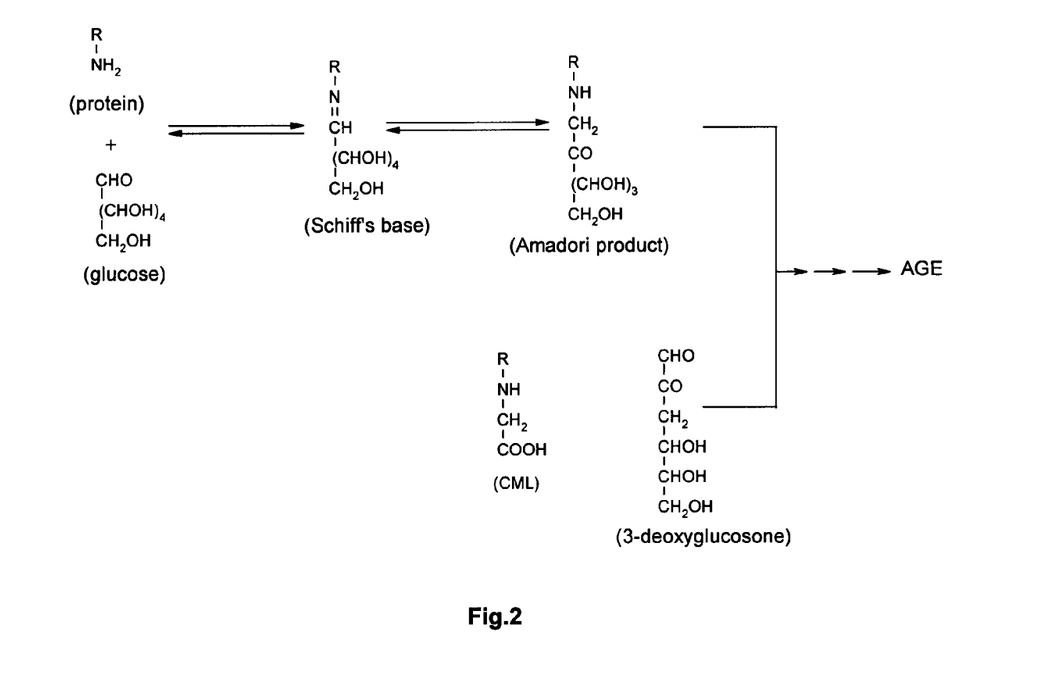
FIG. 2 shows the Maillard route.

AGEs are formed after a complex cascade of reactions that begins with the binding of reducing sugars to proteins: a sugar, in open form, reacts first with the free amine group of basic amino acids present in the proteins (lysine, arginine), leading to the formation of a Schiffs base, which is subsequently stabilised as an Amadori product. FIG. 2 illustrates the Maillard route.

These steps are reversible and dependent on the concentration of the substrates (proteins and sugars). Once formed, the Amadori product undergoes a series of changes that leads either to oxidative fragmentation and to the formation of "glycoxidation" products, such as carboxymethyllysine (CML), or to the formation of dicarbonyls, such as 3-deoxyglucosone, which may in turn react with the free amines of proteins and thus propagate the Maillard reaction (Thornalley, *Clin. Lab.* 45, 1999, 261-273). The AGEs formed during the development of diabetes, and which accumulate in the proteins with a long service life, originate from the reaction with glucose, but also from other reactive dicarbonyls derived from glucose, for instance methylglyoxal. Methylglyoxal, formed by the fragmentation of triose phosphates and the oxidation of acetone in the liver (by means of monooxygenases) is increased in the plasma of diabetics (McLellan et al., *Clin. Sci.* 7, 1994, 21-29). Furthermore, the AGEs of proteins formed after reaction with methylglyoxal are described as major products observed during diabetes (Degenhardt et al, *Cell. Mol. Biol.* 44, 1998, 1139-1145) and the formation of AGEs on the intracellular proteins with methylglyoxal appears to be a major route of formation in the cells (Nishikawa et al., *Nature* 404, 2000, 787-790); Shinohara et al., *J. Clin. Invest.* 101, 1998, 1142-1147). The present inventors have described AGEs formed from methylglyoxal in FR 00/13640 (WO 02/34201 A2) and shown that they induce apoptosis of the pericytes and that caspase-10 is involved at an early stage in the biochemical cascade leading to the death of the pericytes.

The retinal pericytes are buried in the basal membrane of the capillaries and in contact with the proteins with a long service life that constitute it and which, in diabetic patients, accumulate Amadori products (Schalkwijk et al., *Diabetes* 48, 1999, 2446-2453) and AGEs (Endo et al., Horm. Metab. Res. 33, 2001, 317-322) detectable in the capillaries. The AGE receptors, for instance RAGE (Receptor for Advanced Glycation End-Products) (Brett et al., *Am. J. Pathol.* 143, 1993, 1699-1712; Yonekura et al., *Biochem. J.* 370, 2003, 1097-1109), p. 60 p. 90 (Stitt et al., *Am. J. Pathol.* 150, 1997, 523-531; Chibber et al., *Diabetologia* 40, 1997, 156-164) have been described as being present on the plasma membrane of pericytes. The co-localisation of AGEs and of the AGE receptors present on the retinal pericytes indicates that the AGEs might participate in the death of the pericytes observed in the early stages of retinopathy. The possibility of a direct toxic effect of the AGEs on pericytes arises from experiments performed on animals, in which the intravenous infusion of preformed AGEs in non-diabetic rats causes a 25% reduction in the number of pericytes present in the retinal capillaries after two weeks of treatment (Xu et al., *Graefe's Arch. Clin. Exp. Opthalmol.* 241, 2003, 56-62) with accumulation of the AGEs inside and around the retinal pericytes (Stitt et al., *Am. J. Pathol.* 150, 1997, 523-531). An indirect argument for the effect of AGEs on the death of the retinal pericytes arises from pharmacological studies on animals to test the effect of glycation inhibitors, such as aminoguanidine or pyridoxamine on the progress of retinopathy. The treatment of diabetic rats for 29 weeks with pyridoxamine prevents the death of the pericytes observed in the untreated rats and also the formation of AGEs (N(ε)-(carboxymethyl)lysine) in the retinal capillaries (Stitt et al., *Diabetes* 51, 2002, 2826-2832). Similarly, diabetic rats treated for 26 weeks with aminoguanidine show a reduced accumulation of AGEs in the retinal capillaries and also a slowed progress of retinopathy measured by various markers, such as the loss of the pericytes, microaneurisms and the 80% reduced formation of acellular capillaries (Hammes et al., *Proc. Natl Acad. Sci. USA* 88, 1991, 11555-11558).

Identification of caspase-10 in the biochemical cascade leading to the AGE-induced apoptosis of pericytes and the use of specific inhibitors forming the subject of the present invention would make it possible to treat or prevent diabetic retinopathy at an early stage by slowing down the loss of pericytes by apoptosis and also the progress of retinopathy towards the clinical stages of "proliferative retinopathy". It should be pointed out, however, that (a) the caspase-10 inhibitors that are the subject of the invention offer a means of treatment or prevention both of basal retinopathy (less than two microaneurisms per ocular fundus, and of clinically established retinopathy, and that (b) the term "diabetic retinopathy" used in the invention denotes both basal retinopathy and clinically established retinopathy.

Compounds similar to the compounds of the invention have been described in *J. Am. Chem. Soc.* 1955, 2325; DE 1815 802; JP 5 612 5333, *J. Med. Chem.* 1981, 24, 1006-10; JP 5 612 5333, JP 5 612 5338, *Chem. Ind.* 1980, 888-9; *Compt. Rend.* 1964, 258, 943-6; *Can. J. Chem.* 1992, 70, 1237-49; Helv. Chim. Acta 1989, 72, 1690-6; *J. Indian Chem. Soc.* 1936, 13, 593; these compounds form the subject of a disclaimer. However, none of these documents describes the use for the treatment of retinopathy.

According to a first subject, the present invention relates to the use of the compounds of the general formula (I):

for the preparation of a medicament for the prevention and/or treatment of retinopathy.

In the general formula (I):

X, Y and Z, which may be identical or different, each independently represent a —CH= group or a nitrogen atom;

m is an integer chosen from 0, 1, 2, 3, 4 and 5;

n is an integer chosen from 0, 1, 2, 3 and 4;

R1 represents a group chosen from —COOR, —CH$_2$CN, —CH$_2$OH and —CH$_2$COOR, in which R represents a hydrogen atom or a group chosen from -alkyl optionally substituted by a halogen atom or by a group chosen from —OH, —CN, —OAlk, -Aryl, —OR', —NO$_2$, —NRR', -alkylaryl and -perhaloalkyl, or R represents an -aryl, -alkylaryl or -heteroaryl group, each optionally substituted by a halogen atom or by a group chosen from —OR, —CN, -Aryl, —NO$_2$, —NRR', -alkylaryl and -perhaloalkyl;

in which

R' represents an -alkyl group optionally substituted by a halogen atom or by a group chosen from —OR, —CN, —COOR, —NRR', —NO$_2$, -aryl, -alkylaryl and perhaloalkyl;

each of the R2, which may be identical or different, independently represents a halogen atom or a group chosen from —OR', —NO$_2$, —NRCOR', optionally perhalogenated -alkyl, —OH, —CN, —NRR', —COOR, -alkylaryl, -heteroaryl, -aryl or an alkyl group substituted by a halogen atom or by a group —OR, —CN, —COOR, —NRR', —NO$_2$, -aryl, -alkylaryl or perhaloalkyl;

each of the R3, which may be identical or different, independently represents a halogen atom or a group chosen from optionally perhalogenated -alkyl, optionally perhalogenated —Oalkyl, —S(O)$_p$alkyl, —NRR', —OR, —CN, —COOR, —NO$_2$, -aryl, -alkylaryl, or an -alkyl group each optionally substituted by a halogen atom or by a group chosen from —OR, —CN, —COOR, —NRR', —NO$_2$, -aryl, -alkylaryl and perhaloalkyl;

in which p=0, 1 or 2;

and also the tautomeric forms, enantiomers, diastereoisomers and epimers, and the pharmaceutically acceptable salts.

Preferably, R3 is in the para position relative to the phenyl nucleus.

Preferably, R2 is in the para position relative to the phenyl nucleus.

Preferably, m=0, 1 or 2; more preferentially 1.

Preferably, n=0 or 1; more preferentially 1.

Preferably, X, Y and Z each represents a —CH= group.

Preferably, only one from among X, Y and Z represents a nitrogen atom, the other two represent a —CH= group.

Preferably, R1 represents a —COOH, —COOalkyl, —CH$_2$COOH, —CH$_2$CN or —CH$_2$OH group; even more preferably, R1 represents a —COOH group.

Preferably, each of the R2, which may be identical or different, independently represents a halogen atom or a group chosen from —Oalkyl, -perhaloalkyl, —NO$_2$ and —NHCOalkyl; even more preferably, R2 represents a halogen atom.

Preferably, each of the R3, which may be identical or different, independently represents a hydrogen atom or a halogen atom or an -alkyl, —SO$_2$alkyl, —Nalkylalkyl', —Oalkyl, perhaloalkyl or —Operhaloalkyl group. Even more preferably, m=1, R3 is in the para position relative to the phenyl nucleus, and represents a halogen atom or an -alkyl, -perhaloalkyl or —Oalkyl group.

As compounds that are useful according to the invention, mention may be made especially of the compounds chosen from the following compounds:
(4'-methylbiphenyl-2-yl)acetic acid
[4'-(methylsulfonyl)biphenyl-2-yl]acetic acid
[4'-(dimethylamino)biphenyl-2-yl]acetic acid
(2-pyridin-3-ylphenyl)acetic acid
(2-pyridin-4-ylphenyl)acetic acid
[4-chloro-4'-(methylsulfonyl)biphenyl-2-yl]acetic acid
[4-chloro-4'-(dimethylamino)biphenyl-2-yl]acetic acid
(5-chloro-2-pyridin-3-ylphenyl)acetic acid
(5-chloro-2-pyridin-4-ylphenyl)acetic acid
(5-methoxy-2-pyridin-3-ylphenyl)acetic acid
(5-methoxy-2-pyridin-4-ylphenyl)acetic acid
(4-chloro-4'-methylbiphenyl-2-yl)acetic acid
(4-chloro-4'-fluorobiphenyl-2-yl)acetic acid
(4,4'-dichlorobiphenyl-2-yl)acetic acid
[4-chloro-4'-(trifluoromethyl)biphenyl-2-yl]acetic acid
(4-chloro-4'-methoxybiphenyl-2-yl)acetic acid
(4'-tert-butyl-4-chlorobiphenyl-2-yl)acetic acid
(3',4-dichlorobiphenyl-2-yl)acetic acid
[4-chloro-4'-(trifluoromethoxy)biphenyl-2-yl]acetic acid
[4,4'-bis(trifluoromethyl)biphenyl-2-yl]acetic acid
(2'-propoxybiphenyl-2-yl)acetic acid
(5'-chloro-2'-ethoxybiphenyl-2-yl)acetic acid
ethyl [4'-(trifluoromethyl)biphenyl-2-yl]acetate
[4'-(trifluoromethyl)biphenyl-2-yl]acetic acid
(4-fluorobiphenyl-2-yl)acetic acid
(4-fluoro-4'-methylbiphenyl-2-yl)acetic acid
(4,4'-difluorobiphenyl-2-yl)acetic acid
(4-fluoro-4'-methoxybiphenyl-2-yl)acetic acid
[4-fluoro-4'-(trifluoromethyl)biphenyl-2-yl]acetic acid
[4-fluoro-4'-(methylsulfonyl)biphenyl-2-yl]acetic acid
(4'-chloro-4-fluorobiphenyl-2-yl)acetic acid
[4'-(dimethylamino)-4-fluorobiphenyl-2-yl]acetic acid
(4-methoxybiphenyl-2-yl)acetic acid
(4-methoxy-4'-methylbiphenyl-2-yl)acetic acid
(4'-fluoro-4-methoxybiphenyl-2-yl)acetic acid
(4,4'-dimethoxybiphenyl-2-yl)acetic acid
[4-methoxy-4'-(trifluoromethyl)biphenyl-2-yl]acetic acid
[4-methoxy-4'-(methylsulfonyl)biphenyl-2-yl]acetic acid
[4'-(dimethylamino)-4-methoxybiphenyl-2-yl]acetic acid
(5-fluoro-2-pyridin-3-ylphenyl)acetic acid
(5-fluoro-2-pyridin-4-ylphenyl)acetic acid
(4'-methyl-4-nitrobiphenyl-2-yl)acetic acid
(4'-methoxy-4-nitrobiphenyl-2-yl)acetic acid
(4'-chloro-4-nitrobiphenyl-2-yl)acetic acid
[4-nitro-4'-(trifluoromethyl)biphenyl-2-yl]acetic acid
[4-(acetylamino)-4'-methoxybiphenyl-2-yl]acetic acid
[4-(acetylamino)-4'-chlorobiphenyl-2-yl]acetic acid
[4-(acetylamino)biphenyl-2-yl]acetic acid
[4-(acetylamino)-4'-(trifluoromethyl)biphenyl-2-yl]acetic acid
[4-(acetylamino)-4'-methylbiphenyl-2-yl]acetic acid
2-(4-chlorobiphenyl-2-yl)ethanol
2-(4'-chlorobiphenyl-2-yl)ethanol
3-(4-chlorobiphenyl-2-yl)propanenitrile
3-(4-chlorobiphenyl-2-yl)propanoic acid and also the tautomeric forms, enantiomers, diastereoisomers and epimers, and the pharmaceutically acceptable salts.

As compounds that are useful according to the invention, the compounds chosen from the following compounds are especially preferred:
(4-chloro-4'-methylbiphenyl-2-yl)acetic acid
(4,4'-dichlorobiphenyl-2-yl)acetic acid
[4-chloro-4'-(trifluoromethyl)biphenyl-2-yl]acetic acid
(4-chloro-4'-methoxybiphenyl-2-yl)acetic acid and also the tautomeric forms, enantiomers, diastereoisomers and epimers, and the pharmaceutically acceptable salts.

Preferably, the retinopathy is diabetic retinopathy. Even more preferably, the retinopathy is in its early stage.

According to another aspect, the present invention also relates to the use of a compound of the formula (I) for the preparation of a medicament for specifically inhibiting caspase-10 in a patient in need thereof, preferably newly diagnosed diabetic patients and/or patients suffering from early retinopathy.

According to a preferred aspect, the said medicament is suitable for the prevention and/or treatment of the microvascular complications of diabetes, preferably retinopathy.

According to another subject, the present invention also relates to the novel compounds of the general formula (II):

in which:
X, Y and Z, which may be identical or different, each independently represent a —CH= group or a nitrogen atom;
m is an integer chosen between 0, 1, 2, 3, 4 and 5;
R1 represents a group chosen from —COOR, —CH$_2$CN, —CH$_2$OH and —CH$_2$COOR,
in which
R represents a hydrogen atom or a group chosen from -alkyl optionally substituted by a halogen atom or by a group chosen from —OH, —CN, —OAlkyl, -Aryl, —OR', NO$_2$, —NRR', -alkylaryl and -perhaloalkyl,
or R represents an -aryl, -alkylaryl or -heteroaryl group, each optionally substituted by a halogen atom or by a group chosen from —OR, —CN, -Aryl, NO$_2$, —NRR', -alkylaryl and -perhaloalkyl;
in which R' represents an -alkyl group optionally substituted by a halogen atom or by a group chosen from —OR, —CN, —COOR, —NRR', —NO$_2$, -aryl, -alkylaryl and perhaloalkyl;
R2 represents a halogen atom or a group chosen from —OR', —NO$_2$, —NRCOR', optionally perhalogenated -alkyl, —OH, —CN, —COOR, -alkylaryl, or an alkyl group substituted by a halogen atom or by a group —OR, —CN, —NRR', —COOR, —NO$_2$, -aryl, -alkylaryl or perhaloalkyl;
each of the R3, which may be identical or different, independently represents a halogen atom or a group chosen from optionally perhalogenated -alkyl, optionally perhalogenated —Oalkyl, —S(O)$_p$alkyl, —NRR', —OR, —CN, —NO$_2$, -aryl, -alkylaryl, or an -alkyl group, each optionally substituted by a halogen atom or by a group chosen from —OR, —CN, —NRR', —NO$_2$, -aryl, -alkylaryl and perhaloalkyl;
in which p=0, 1 or 2;
and also the tautomeric forms, enantiomers, diastereoisomers and epimers, and the pharmaceutically acceptable salts,
with the exception of the compounds of the general formula (I) for which:
if X=Y=C,
R2=—Cl,
R1=—CO$_2$H, m=0, or
R1=—CO$_2$H, m=2 and R3=(2-Cl, 6-Cl);

R2=-OMe
R1=—CO$_2$H or —CO$_2$Me, m=1 and R3=4-Cl, or
R1=—CH$_2$OH, m=0, or
R1=CH$_2$CO$_2$H, m=2, and R3=(3-OMe, 2-OMe) or (3-OMe, 4-OMe), or
R1=CH$_2$CO$_2$H, m=3 and R3=(2-OMe, 3-OMe, 4-OMe);
R2=-Me
R1=CO$_2$Et, m=0.

Preferably, R3 is in the para position relative to the phenyl nucleus.
Preferably, m=0, 1 or 2; more preferably 1.
Preferably, X, Y and Z each represent a —CH= group.
Preferably, only one from among X, Y and Z represents a nitrogen atom, the other two representing a —CH= group.
Preferably, R1 represents a —COOH, —COOalkyl, —CH$_2$COOH, —CH$_2$CN or —CH$_2$OH group; even more preferably, R1 represents a —COOH group.
Preferably, R2 represents a halogen atom or a group chosen from —Oalkyl, -perhaloalkyl, —NO$_2$ and —NHCOalkyl; even more preferably, R2 represents a halogen atom.
Preferably, each of the R3, which may be identical or different, independently represents a halogen atom or an -alkyl, —SO$_2$alkyl, —Nalkylalkyl, —Oalkyl, perhaloalkyl or —Operhaloalkyl group. Even more preferably, m=1, R3 is in the para position relative to the phenyl nucleus, and represents a halogen atom or an -alkyl, -perhaloalkyl or —Oalkyl group.

As compounds according to the invention, mention may be made especially of the compounds chosen from the following compounds:
[4-chloro-4'-(methylsulfonyl)biphenyl-2-yl]acetic acid
[4-chloro-4'-(dimethylamino)biphenyl-2-yl]acetic acid
(5-chloro-2-pyridin-3-ylphenyl)acetic acid
(5-chloro-2-pyridin-4-ylphenyl)acetic acid
(5-methoxy-2-pyridin-3-ylphenyl)acetic acid
(5-methoxy-2-pyridin-4-ylphenyl)acetic acid
(4-chloro-4'-methylbiphenyl-2-yl)acetic acid
(4-chloro-4'-fluorobiphenyl-2-yl)acetic acid
(4,4'-dichlorobiphenyl-2-yl)acetic acid
[4-chloro-4'-(trifluoromethyl)biphenyl-2-yl]acetic acid
(4-chloro-4'-methoxybiphenyl-2-yl)acetic acid
(4'-tert-butyl-4-chlorobiphenyl-2-yl)acetic acid
(3',4-dichlorobiphenyl-2-yl)acetic acid
[4-chloro-4'-(trifluoromethoxy)biphenyl-2-yl]acetic acid
[4,4'-bis(trifluoromethyl)biphenyl-2-yl]acetic acid
(4-fluorobiphenyl-2-yl)acetic acid
(4-fluoro-4'-methylbiphenyl-2-yl)acetic acid
(4,4'-difluorobiphenyl-2-yl)acetic acid
(4-fluoro-4'-methoxybiphenyl-2-yl)acetic acid
[4-fluoro-4'-(trifluoromethyl)biphenyl-2-yl]acetic acid
[4-fluoro-4'-(methylsulfonyl)biphenyl-2-yl]acetic acid
(4'-chloro-4-fluorobiphenyl-2-yl)acetic acid
[4'-(dimethylamino)-4-fluorobiphenyl-2-yl]acetic acid
(4-methoxybiphenyl-2-yl)acetic acid
(4-methoxy-4'-methylbiphenyl-2-yl)acetic acid
(4'-fluoro-4-methoxybiphenyl-2-yl)acetic acid
(4,4'-dimethoxybiphenyl-2-yl)acetic acid
[4-methoxy-4'-(trifluoromethyl)biphenyl-2-yl]acetic acid
[4-methoxy-4'-(methylsulfonyl)biphenyl-2-yl]acetic acid
[4'-(dimethylamino)-4-methoxybiphenyl-2-yl]acetic acid
(5-fluoro-2-pyridin-3-ylphenyl)acetic acid
(5-fluoro-2-pyridin-4-ylphenyl)acetic acid
(4'-methyl-4-nitrobiphenyl-2-yl)acetic acid
(4'-methoxy-4-nitrobiphenyl-2-yl)acetic acid
(4'-chloro-4-nitrobiphenyl-2-yl)acetic acid
[4-nitro-4'-(trifluoromethyl)biphenyl-2-yl]acetic acid
[4-(acetylamino)-4'-methoxybiphenyl-2-yl]acetic acid

[4-(acetylamino)-4'-chlorobiphenyl-2-yl]acetic acid
[4-(acetylamino)biphenyl-2-yl]acetic acid
[4-(acetylamino)-4'-(trifluoromethyl)biphenyl-2-yl]acetic acid
[4-(acetylamino)-4'-methylbiphenyl-2-yl]acetic acid
2-(4-chlorobiphenyl-2-yl)ethanol
2-(4'-chlorobiphenyl-2-yl)ethanol
3-(4-chlorobiphenyl-2-yl)propanenitrile
3-(4-chlorobiphenyl-2-yl) propanoic acid and also the tautomeric forms, enantiomers, diastereoisomers and epimers, and the pharmaceutically acceptable salts.

As compounds according to the invention, the compounds chosen from the following compounds are especially preferred:
(4-chloro-4'-methylbiphenyl-2-yl)acetic acid
(4,4'-dichlorobiphenyl-2-yl)acetic acid
[4-chloro-4'-(trifluoromethyl)biphenyl-2-yl]acetic acid
(4-chloro-4'-methoxybiphenyl-2-yl)acetic acid and also the tautomeric forms, enantiomers, diastereoisomers and epimers, and the pharmaceutically acceptable salts.

According to the present invention, the alkyl radicals represent saturated hydrocarbon-based radicals, in a straight or branched chain, of 1 to 20 carbon atoms and preferably of 1 to 5 carbon atoms.

If they are linear, mention may be made especially of methyl, ethyl, propyl, butyl, pentyl, hexyl, octyl, nonyl, decyl, dodecyl, hexadecyl and octadecyl radicals.

If they are branched or substituted by one or more alkyl radicals, mention may be made especially of isopropyl, tert-butyl, 2-ethylhexyl, 2-methylbutyl, 2-methylpentyl, 1-methylpentyl and 3-methylheptyl radicals.

The term "perhaloalkyl" means alkyl groups in which all the hydrogen atoms are replaced with a halogen atom. The —$CF_3$ radical is especially preferred.

The alkoxy radicals according to the present invention are radicals of the formula —O-alkyl, the alkyl being as defined above. Similarly, the term "perhalogenated —Oalkyl" or "—Operhaloalkyl" means an alkoxy group in which all the hydrogens of the alkyl group have been replaced with a halogen atom; the —$OCF_3$ group is especially preferred.

Among the halogen atoms that are more particularly mentioned are fluorine, chlorine, bromine and iodine atoms, preferably fluorine.

The alkenyl radicals represent hydrocarbon-based radicals in a straight or linear chain, and comprise one or more ethylenic unsaturations. Among the alkenyl radicals that may especially be mentioned are allyl or vinyl radicals.

The alkynyl radicals represent hydrocarbon-based radicals, in a straight or linear chain, and comprise one or more acetylenic unsaturations. Among the alkynyl radicals, mention may be made especially of acetylene.

The cycloalkyl radical is a saturated or partially unsaturated, non-aromatic mono-, bi- or tricyclic hydrocarbon-based group of 3 to 10 carbon atoms, especially, such as cyclopropyl, cyclopentyl, cyclohexyl or adamantyl, and also the corresponding rings containing one or more unsaturations.

Aryl or Ar denotes a monocyclic or bicyclic hydrocarbon-based aromatic system of 6 to 10 carbon atoms.

Among the aryl radicals that may especially be mentioned are phenyl and naphthyl radicals.

Among the -alkylaryl radicals, mention may be made especially of benzyl and phenethyl radicals.

Het denotes a heteroaryl group; the heteroaryl radicals denote monocyclic or bicyclic aromatic systems of 5 to 10 carbon atoms, comprising one or more hetero atoms chosen from nitrogen, oxygen and sulfur. Among the heteroaryl radicals that may be mentioned are pyrazinyl, thienyl, oxazolyl, furazanyl, pyrrolyl, 1,2,4-thiadiazolyl, naphthyridinyl, pyridazinyl, quinoxalinyl, phthalazinyl, imidazo[1,2-a]pyridine, imidazo[2,1-b]thiazolyl, cinnolinyl, triazinyl, benzofurazanyl, azaindolyl, benzimidazolyl, benzothienyl, thienopyridyl, thienopyrimidinyl, pyrrolopyridyl, imidazopyridyl, benzazaindole, 1,2,4-triazinyl, benzothiazolyl, furanyl, imidazolyl, indolyl, triazolyl, tetrazolyl, indolizinyl, isoxazolyl, isoquinolinyl, isothiazolyl, oxadiazolyl, pyrazinyl, pyridazinyl, pyrazolyl, pyridyl, pyrimidinyl, purinyl, quinazolinyl, quinolinyl, isoquinolyl, 1,3,4-thiadiazolyl, thiazolyl, triazinyl, isothiazolyl and carbazolyl, and also the corresponding groups derived from their fusion or from fusion with the phenyl nucleus. The preferred heteroaryl groups comprise thienyl, pyrrolyl, quinoxalinyl, furanyl, imidazolyl, indolyl, isoxazolyl, isothiazolyl, pyrazinyl, pyridazinyl, pyrazolyl, pyridyl, pyrimidinyl, quinazolinyl, quinolinyl, thiazolyl, carbazolyl and thiadiazolyl, and groups derived from fusion with a phenyl nucleus, and more particularly quinolinyl, carbazolyl and thiadiazolyl.

The expression "pharmaceutically acceptable salts" refers to the relatively non-toxic mineral and organic acid-addition salts, and the base-addition salts, of the compounds of the present invention. These salts can be prepared in situ during the final isolation and purification of the compounds. In particular, the acid-addition salts can be prepared by separately reacting the purified compound in its purified form with an organic or mineral acid and isolating the salt thus formed. Among the examples of acid-addition salts are the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, sulfamates, malonates, salicylates, propionates, methylenebis-b-hydroxynaphthoates, gentisic acid, isethionates, di-p-toluoyltartrates, methanesulfonates, ethanesulfonates, benzenesulfonates, p-toluenesulfonates, cyclohexyl sulfamates and quinates-laurylsulfonate, and analogues. (See for example S. M. Berge et al. "Pharmaceutical Salts" *J. Pharm. Sci,* 66: pp. 1-19 (1977) which is incorporated herein by reference). The acid-addition salts can also be prepared by separately reacting the purified compound in its acid form with an organic or mineral base and isolating the salt thus formed. The acid-addition salts include amine salts and metal salts. The suitable metal salts include the sodium, potassium, calcium, barium, zinc, magnesium and aluminium salts. The sodium and potassium salts are preferred. The suitable mineral base-addition salts are prepared from metallic bases including sodium hydride, sodium hydroxide, potassium hydroxide, calcium hydroxide, aluminium hydroxide, lithium hydroxide, magnesium hydroxide and zinc hydroxide. The suitable amine base-addition salts are prepared from amines whose basicity is sufficient to form a stable salt, and preferably include amines that are often used in medicinal chemistry on account of their low toxicity and their acceptability for medical use: ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, for example lysine and arginine, and dicyclohexylamine, and analogues.

The term "precursor group" means any chemical function allowing the desired chemical function to be formed by means of one or more suitable chemical reactions referred to herein as "derivatisation reactions".

The invention also relates to the tautomeric forms, enantiomers, diastereoisomers, epimers and organic or mineral salts of the compounds of the general formula (I).

The compounds of the invention of the formula (I) as defined above containing a sufficiently acidic function or a sufficiently basic function, or both, may include the corresponding pharmaceutically acceptable salts of an organic or mineral acid or of an organic or mineral base.

The compounds of the general formulae (I) and (II) can be prepared by application or adaptation of any method known per se and/or within the capacity of a person skilled in the art, especially those described by Larock in *Comprehensive Organic Transformations*, VCH Pub., 1989, or by application or adaptation of the processes described in the examples that follow.

According to another subject, the present invention also relates to the process for the preparation of the compounds of the formula (II) as defined above.

It is understood that the compounds of the formula (I) can be prepared via a similar process, starting with suitable starting materials.

According to the invention, the process for the preparation of a compound of the formula (II) includes the step of preparing a corresponding compound of the formula (II'):

(II')

in which X, Y, Z and m are as defined above and R1', R2' and R3' represent, respectively, R1, R2 and R3 or a precursor group of R1, R2 and R3, by Suzuki coupling, by means of a compound of the formula (III) and a compound of the formula (IV):

(III)

(IV)

in which X, Y, Z, m, R1', R2' and R3' are as defined above, each of the R represents a hydrogen atom or an alkyl group, or the R form, with the boron atom to which they are attached, a group:

and T represents a triflate group (—OTf) or a halogen atom, preferably bromine.

Generally, this reaction is performed by palladium catalysis, especially using a catalyst, such as $(PPh_3)_4Pd$, $Pd(dppf)Cl_2$ or $Pd(OAc)_2+PPh_3$, in basic medium, such as $Na_2CO_3$, EtONa, $Et_3N$, $K_3PO_4$, TlOH or $Ba(OH)_2$, especially in a solvent medium, such as methanol, benzene, water or THF, alone or as a mixture.

Preferably, the reaction mixture is heated to a temperature of between 25° C. and the reflux temperature of the mixture.

The process according to the invention may also include the subsequent step of separating out and/or purifying the product of the formula (II) obtained.

If, in formula (II'), R1', R2' and/or R3' represents a precursor of R1, R2 or R3, respectively, the process according to the invention also includes the subsequent step for converting, respectively, R1', R2' and/or R3' into R1, R2 and/or R3 so as to obtain the desired compound of the formula (II).

These derivatisation reactions are generally known per se and within the scope of a person skilled in the art.

The process according to the invention then includes the step consisting in converting the product of the formula (II') obtained (II')

into the desired product of the formula (II).

As an illustration, if, in compound (II'), R1' represents a —$CO_2$alkyl or —$CO_2$Pol group in which Pol represents a solid support, such as a resin, the desired compound of the formula (II) in which R1 represents a —$CO_2$H group can be obtained by saponification or hydrolysis.

Preferably, the saponification is performed in basic medium, for example in the presence of sodium hydroxide or KOH. Hydrolysis of the resin is performed especially using an acid, such as trifluoroacetic acid.

If, in formula (II'), R1' represents a —$CO_2$alkyl group, the desired compound of the formula (II) in which R1 represents a —$CH_2OH$ group can be obtained by reduction. It is especially preferred to work using a reducing agent, such as $LiAlH_4$, $NaBH_4$, $SiHCl_3$, $NaBH(OMe)_3$, $BH_3$-$Me_2S$, etc.

The compounds of the formula (II) in which R1=—CH$_2$CN can be obtained from the corresponding compounds of the formula (II) in which R1=—CH$_2$OH, by halogenation of the —CH$_2$OH group to —CH$_2$Hal followed by nucleophilic substitution of the halogen atom with the —CN group.

Preferably, the halogenation reaction is performed using a reagent of the PHal$_3$ type, especially PBr$_3$ or PCl$_3$, or alternatively using reagents, such as SOCl$_2$, PPh$_3$/CBr$_4$, SOBr$_2$, PPh$_3$/NBS, HBr, PBr$_5$, TMSCl, PCl$_5$ or ZnCl$_2$/HCl.

Preferably, the nucleophilic substitution reaction is performed using the reagent NaCN, KCN, Et$_2$$^+$CN$^-$, LiCN or TMS-CN.

The compounds of the formula (II) in which R1 represents a —CH$_2$COOH group can be obtained from the corresponding compounds of the formula (II) in which R1=—CH$_2$CN by conversion of the —CN group into a carboxyl group —CO$_2$H.

Preferably, this reaction is performed in basic medium in the presence of ethanol and water.

The compounds of the formula (II) in which R1=—CH$_2$CO$_2$alkyl can then be obtained from the corresponding compounds of the formula (II) in which R1=—CH$_2$CO$_2$H by esterification using the corresponding alcohol alkyl-OH.

Similarly, the compounds of the formula (II) can be obtained from the corresponding compounds (II') in which R2' and/or R3' represent a precursor function of the desired group R2 and/or R3 by derivatisation of the group R2' and/or R3' via methods that are known per se.

By way of illustration, the compounds of the formula (II) in which R2 represents the group —NRCOR' in which R and R' are as defined in formula (II) can be obtained from the corresponding compounds of the formula (II') in which R2' represents an —NO$_2$ group, by catalytic hydrogenation of the —NO$_2$ group to an —NH$_2$ group, followed by amidation.

Needless to say, the appropriate derivatisation reactions can be performed by application or adaptation of methods that are known per se, within the scope of a person skilled in the art.

Route A (Examples 1 to 24)

Route B (Examples 25 to 45)

Route C (Examples 46 to 50)

Route D (Examples 51 and 52)

Route E (Examples 53 and 54)

In the reactions described hereinabove, it may be necessary to protect reactive functional groups, for example the hydroxyl, amino, imino, thio or carboxyl groups, if they are desired in the final product, to avoid their unwanted participation in the reactions. The conventional protecting groups can be used in accordance with standard practice; for examples, see T. W. Green and P. G. M. Wuts in *Protective Groups in Organic Chemistry*, John Wiley and Sons, 1991; J. F. W. McOmie in *Protective Groups in Organic Chemistry*, Plenum Press, 1973.

The compound of the formula (II) thus prepared can be recovered from the reaction mixture by conventional means. For example, the compounds can be recovered by distilling the solvent from the reaction mixture or, if necessary, after distilling off the solvent from the mixture of the solution, pouring the remainder into water, followed by extraction with a water-immiscible organic solvent, and distilling the solvent from the extract. In addition, the product can also be purified, if so desired, by various techniques, such as recrystallisation, reprecipitation or various chromatographic techniques, especially column chromatography or preparative thin-layer chromatography.

It will be appreciated that the compounds that are useful according to the present invention may contain asymmetric centres. These asymmetric centres may be, independently, of R or S configuration. It will be apparent to a person skilled in the art that certain compounds that are useful according to the invention may also exhibit geometrical isomerism. It should be understood that the present invention includes individual geometrical isomers and stereoisomers, and mixtures thereof, including racemic mixtures, of compounds of the formula (I) or (II) above. Isomers of this type can be separated from their mixtures by application or adaptation of known processes, for example chromatography techniques or recrystallisation techniques, or they are prepared separately from suitable isomers of their intermediates.

For the purposes of the present text, it is understood that the tautomeric forms are included in the citation of a given group, for example thio/mercapto or oxo/hydroxyl.

The acid-addition salts are formed with the compounds that are useful according to the invention in which a basic function, such as an amino, alkylamino or dialkylamino group is present. The pharmaceutically acceptable, i.e. non-toxic, acid-addition salts are preferred. The selected salts are optimally chosen so as to be compatible with the usual pharmaceutical vehicles and suitable for oral or parenteral administration. The acid-addition salts of the compounds that are useful according to the present invention can be prepared by reacting the free base with the appropriate acid, by application or adaptation of known processes. For example, the acid-addition salts of the compounds that are useful according to the pre-sent invention can be prepared either by dissolving the free base in water or in a basified aqueous solution or suitable solvents containing the appropriate acid, and isolating the solvent by evaporating the solution, or by reacting the free base and the acid in an organic solvent, in which case the salt separates out directly or can be obtained by concentrating the solution. Among the acids that are suitable for use in the preparation of these salts are hydrochloric acid, hydrobromic acid, phosphoric acid, sulfuric acid, various organic carboxylic and sulfonic acids, such as acetic acid, citric acid, propionic acid, succinic acid, benzoic acid, tartaric acid, fumaric acid, mandelic acid, ascorbic acid, malic acid, methanesulfonic acid, toluenesulfonic acid, fatty acids, adipate, alginate, ascorbate, aspartate, benzenesulfonate, benzoate, cyclopentanepropionate, digluconate, dodecyl sulfate, bisulfate, butyrate, lactate, laurate, lauryl sulfate, malate, hydriodide, 2-hydroxyethanesulfonate, glycerophosphate, picrate, pivalate, pamoate, pectinate, persulfate, 3-phenylpropionate, thiocyanate, 2-naphthalenesulfonate, undecanoate, nicotinate, hemisulfate, heptonate, hexanoate, camphorate, camphorsulfonate and the like.

The acid-addition salts of the compounds that are useful according to the present invention can be regenerated from the salts by application or adaptation of known processes. For example, the parent compounds that are useful according to the invention can be regenerated from their acid-addition salts by treatment with an alkali, for example aqueous sodium bicarbonate solution or aqueous ammonia solution.

The compounds that are useful according to the present invention can be regenerated from their base-addition salts by application or adaptation of known processes. For example, the parent compounds that are useful according to the invention can be regenerated from their base-addition salts by treatment with an acid, for example hydrochloric acid.

The base-addition salts may be formed if the compound that is useful according to the invention contains a carboxyl group, or a sufficiently acidic bio-isostere. The bases that can be used to prepare the base-addition salts preferably include those that produce, if they are combined with a free acid, pharmaceutically acceptable salts, i.e. salts whose cations are not toxic to the patient in the pharmaceutical doses of the salts, such that the beneficial inhibitory effects intrinsic to the free base are not negated by the side effects attributable to the cations. The pharmaceutically acceptable salts, including those derived from alkaline-earth metal salts, within the scope of the present invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl) aminomethane, tetramethylammonium hydroxide and the like.

The compounds that are useful according to the present invention can be readily prepared, or formed during the process of the invention, in the form of solvates (for example hydrates). The hydrates of the compounds that are useful according to the present invention can be readily prepared by recrystallisation of an aqueous/organic solvent mixture, using organic solvents, such as dioxane, tetrahydrofuran or methanol.

According to another subject, the present invention also relates to pharmaceutical compositions comprising a compound of the general formula (II) as defined above and pharmaceutically acceptable excipient.

Preferably, the said composition comprises an effective amount of the compound according to the invention.

Preferably, the said composition is administered to a patient in need thereof.

The pharmaceutical compositions according to the invention can be presented in forms intended for parenteral, oral, rectal, permucous or percutaneous administration.

They will thus be presented in the form of injectable solutions or suspensions or multi-dose bottles, in the form of plain or coated tablets, sugar-coated tablets, wafer capsules, gel capsules, pills, sachets, powders, suppositories or rectal capsules, solutions or suspensions, for percutaneous use in a polar solvent, or for permucous use.

The excipients that are suitable for such administrations are cellulose or microcrystalline cellulose derivatives, alkaline-earth metal carbonates, magnesium phosphate, starches, modified starches and lactose for solid forms.

For rectal use, cocoa butter or polyethylene glycol stearates are the preferred excipients.

For parenteral use, water, aqueous solutions, physiological saline and isotonic solutions are the vehicles most appropriately used.

The dosage can vary within wide ranges (0.5 mg to 1000 mg) depending on the therapeutic indication and the route of administration, and also on the age and weight of the patient.

The base products or the reagents used are commercially available and/or can be prepared by application or adaptation of known processes, for example processes as described in the Reference Examples or obvious chemical equivalents thereof.

The examples that follow are given as non-limiting illustrations of the pre-sent invention. The starting materials are commercially available or can be pre-pared via processes that are known per se.

The frequency of the NMR machine used to record the proton spectra of the examples given below is 300 MHz. The abbreviation s denotes a singlet; d a doublet; t a triplet; q a quartet and m a multiplet. The values are expressed in ppm.

The LC-MS spectra are obtained on a simple quadrupole machine equipped with an electrospray probe.

EXAMPLE 1

(4'-Methylbiphenyl-2-yl)acetic acid a) Ethyl (4'-methylbiphenyl-2-yl)acetate

To a mixture composed of 243.1 mg (1 mmol) of ethyl 2-(2-bromophenyl)acetate, 3.7 ml of toluene, 57.8 mg (0.05 mmol) of tetrakis(triphenylphosphine)palladium and 127.2 mg (1.2 mmol) of anhydrous sodium carbonate are added 169.9 mg (1.25 mmol) of 4-methylphenylboronic acid, followed by addition of 2.21 ml (0.055 mmol) of methanol. The reaction medium is heated at 85° C. for 16 hours with stirring. After cooling, 10 ml of water and 8 ml of ethyl acetate are added with stirring, and the mixture is then filtered through a fluted filter paper. The organic phase is recovered and the aqueous phase is extracted again with ethyl acetate.

The combined organic phases are washed with water (2×10 ml), dried over $Na_2SO_4$ and then concentrated to give 310 mg of oil, which is purified by flash chromatography on a column of silica, in a dichloromethane/heptane mixture (1:1). 201 mg of a colourless oil are obtained.

Yield: 79%

NMR ($CDCl_3$): 1.2 (t, J=7.2 Hz, 3H); 2.5 (s, 3H); 3.7 (m, 2H), 4.1 (q, J=7.2 Hz, 2H); 7.3 (m, 8H).

b) (4'-Methylbiphenyl-2-yl)acetic acid

A mixture of 201 mg (0.79 mmol) of the compound prepared in Example 1a, 1.581 ml (1.581 mmol) of aqueous KOH solution (1N), 1.5 ml of water and 4 ml of ethanol is maintained at reflux for two hours. After cooling and removal of the ethanol by concentration under vacuum, 10 ml of water are added and the reaction medium is then washed with ether.

The aqueous phase is acidified with 16% HCl. The precipitate formed is recovered by filtration and washed with water. After drying under vacuum, 171 mg of a white solid are obtained.

Yield: 95.6%

NMR (DMSO-$d_6$): 2.3 (s, 3H); 3.5 (s, 2H); 7.2 (m, 8H); 12.2 (s, 1H).

LC-MS: ($ES^-$)=225.2 (M-1)

EXAMPLES 2 TO 22

The compounds of Table 1 were obtained by working as in Example 1a (ester) and 1b (acid).

TABLE 1

| Ex | R2 | X | Y | R3 | NMR | LCMS |
|----|----|----|----|----|----|----|
| 2 | H | CH | CH | 4-MeSO2- | (DMSO-D6) 3.3 (m, 3 H); 3.5 (s, 2 H); 7.4 (m, 6 H); 8.0 (d, J = 8.2 Hz, 2 H); 12.3 (s, 1 H) | (ES−): 289.2 |
| 3 | H | CH | CH | 4-Me2N— | (DMSO-D6) 2.9 (s, 6 H); 3.5 (s, 2 H); 6.8 (d, J = 8.8 Hz, 2 H); 7.2 (m, 6 H); 12.2 (s, 1 H) | (ES+): 256.3 |
| 4 | H | N | CH | H | (DMSO-D6) 3.5 (s, 2 H); 7.5 (m, 6 H); 8.5 (m, 2 H); 12.3 (s, 1 H) | (ES+): 214.1 |
| 5 | H | CH | N | H | (CDCl3) 3.6 (s, 2 H); 7.3 (m, 7 H); 8.6 (broad multiplet, 1 H); 10.4 (broad multiplet, 1 H) | (ES+): 214.1 |
| 6 | Cl | CH | CH | 4-MeSO2- | (DMSO-D6) 3.3 (m, J = 8.2 Hz, 3 H); 7.4 (m, 5 H); 8.0 (d, J = 8.2 Hz, 2 H); 12.4 (s, 1 H) | (ES−): 323.2 |
| 7 | Cl | CH | CH | 4-Me2N— | (DMSO-D6) 2.9 (m, 6 H); 3.5 (m, 2 H); 6.8 (d, J = 8.6 Hz, 2 H); 7.3 (m, 5 H); 12.4 (s, 1 H) | |
| 8 | Cl | N | CH | H | (DMSO-D6) 3.5 (s, 2 H); 7.5 (m, 5 H); 8.6 (m, 2 H); 12.4 (s, 1 H) | (ES−): 248.2/ 250.1 1 chlorine atom |
| 9 | Cl | CH | N | H | (DMSO-D6) 3.6 (s, 2 H); 7.4 (m, 5 H); 8.6 (d, J = 5.7 Hz, 2 H); 12.4 (s, 1 H) | (ES−): 248.1/ 250.1 1 chlorine atom |
| 10 | MeO | N | CH | H | (DMSO-D6) 3.5 (s, 2 H); 3.8 (m, 3 H); 7.3 (m, 5 H); 8.5 (m, 2 H); 12.3 (s, 1 H) | (ES+): 244.2 |
| 11 | MeO | CH | N | H | (DMSO-D6) 3.5 (s, 2 H); 3.8 (d, J = 8.4 Hz, 3 H); 7.1 (m, 5 H); 8.6 (d, J = 5.5 Hz, 2 H); 12.3 (s, 1 H) | (ES+): 244.1 |
| 12 | Cl | CH | CH | 4-Me— | | (ES−): 215.2 217.2 259.2 261.2 1 chlorine atom |
| 13 | Cl | CH | CH | 4-F— | (DMSO-D6) 3.5 (s, 2 H); 7.3 (m, 5 H); 7.4 (dd, J = 8.2, 2.1 Hz, 1 H); 7.5 (d, J = 2.3 Hz, 1 H); 12.4 (s, 1 H) | (ES−): 263.1/ 265.1 1 chlorine atom |
| 14 | Cl | CH | CH | 4-Cl— | (DMSO-D6) 3.5 (s, 2 H); 7.3 (m, 3 H); 7.4 (m, 1 H); 7.5 (m, 3 H); 12.4 (s, 1 H) | (ES−): 279.1/ 281.1/283.1 2 chlorine atoms |
| 15 | Cl | CH | CH | 4-F3C— | (DMSO-D6) 3.6 (s, 2 H); 7.3 (d, J = 8.2 Hz, 1 H); 7.4 (m, 1 H); 7.5 (m, 3 H); 7.8 (d, J = 8.2 Hz, 2 H); 12.4 (s, 1 H) | (ES−): 313.2/ 315.1 1 chlorine atom |
| 16 | Cl | CH | CH | 4-MeO— | (DMSO-D6) 3.5 (s, 2 H); 3.8 (s, 3 H); 7.0 (m, 2 H); 7.2 (m, 3 H); 7.4 (m, 1 H); 7.4 (d, J = 2.1 Hz, 1 H); 12.4 (s, 1 H) | |
| 17 | Cl | CH | CH | 4-tBu- | (DMSO-D6) 1.3 (s, 9 H); 3.5 (s, 2 H); 7.2 (m, 3 H); 7.4 (m, 1 H); 7.5 (m, 3 H); 12.4 (s, 1 H) | (ES−): 301.4/ 303.4 1 chlorine atom |
| 18 | Cl | CH | CH | 3-Cl— | (DMSO-D6) 3.5 (s, 2 H); 7.3 (m, 2 H); 7.3 (d, J = 1.1 Hz, 1 H); 7.4 (m, 1 H); 7.5 (m, 3 H); 12.4 (s, 1 H) | (ES−): 279.3/ 281.3/283.3 2 chlorine atoms |
| 19 | Cl | CH | CH | 4-F3C—O— | (DMSO-D6) 3.5 (s, 2 H); 7.3 (d, J = 8.2 Hz, 1 H); 7.4 (m, 6 H); 12.4 (s, 1 H) | (ES−): 329.3/ 331.3 1 chlorine atom |
| 20 | CF3 | CH | CH | 4-F3C— | (DMSO-D6) 3.7 (s, 2 H); 7.5 (d, J = 7.8 Hz, 1 H); 7.6 (d, J = 8.0 Hz, 7.7 (m, 1 H); 7.8 (m, 3 H); 12.5 (s, 1 H) | |

TABLE 1-continued

| Ex | R2 | X | Y | R3 | NMR | LCMS |
|----|----|----|----|----|-----|------|
| 21 | H | CH | CH | 2-nPrO— | (DMSO-D6) 0.8 (t, J = 7.3 Hz, 3 H); 1.5 (m, 2 H); 3.4 (d, J = 11.6 Hz, 2 H); 3.8 (t, J = 6.4 Hz, 2 H); 7.2 (m, 8 H); 12.0 (s, 1 H) | (ES−): 269.3 |
| 22 | H | CH | CH | 2-EtO-5-Cl— | (DMSO-D6) 1.1 (t, J = 7.0 Hz, 3 H); 3.4 (d, J = 6.7 Hz, 2 H); 4.0 (q, J = 6.9 Hz, 2 H); 7.3 (m, 7 H); 12.1 (s, 1 H) | (ES−): 289.2/ 291.2 1 chlorine atom |

EXAMPLE 23

Ethyl (4'-trifluoromethylbiphenyl-2-yl)acetate

Obtained by working as in Example 1a.

Yield: 70.1%

NMR (CDCl$_3$): 1.1 (t, J=7.2 Hz, 3H); 3.5 (s, 2H); 4.0 (q, J=7.2 Hz, 2H); 7.4 (m, 8H).

EXAMPLE 24

(4'-Trifluoromethylbiphenyl-2-yl)acetic acid

Obtained by working as in Example 1b.

Yield: 73.7%

NMR (DMSO-d$_6$): 3.5 (s, 2H); 7.3 (m, 1H); 7.4 (m, 3H); 7.5 (d, J=8.0 Hz, 2H); 7.8 (d, J=8.0 Hz, 2H); 12.3 (s, 1H).

LC-MS: (ES−): 279.2 (M-1)

EXAMPLE 25

(4-Fluorobiphenyl-2-yl)acetic acid a) 4-(Benzyloxy)benzyl (2-bromo-5-fluorophenyl)acetate resin

A suspension of 3 g (2.73 mmol) of Wang resin (p-benzyloxybenzyl alcohol resin, 100-200 mesh) in 49 ml of dichloromethane is stirred (orbital stirring) at room temperature for 15 minutes. 2.8 g (12.0 mmol) of (2-bromo-5-fluorophenyl) acetic acid dissolved in 20 ml of dichloromethane are then added, followed by addition of 0.067 g (0.55 mmol) of 4-dimethylaminopyridine and 1.88 ml (12.0 mol) of N,N'-diisopropylcarbodiimide.

The reaction medium is stirred for 16 hours at room temperature and then filtered. The resin is then washed with DMF (4×10 ml), THF (4×10 ml), methanol (4×10 ml) and dichloromethane (4×10 ml) and then dried under vacuum at 50° C. 3.59 g of resin with a theoretical charge of 0.76 mM/g are obtained.

b) 4-(Benzyloxy)benzyl (4-fluorobiphenyl-2-yl)acetate resin

To a suspension 197.4 mg (0.15 mmol) of the resin prepared in Example 25a, in 4.5 ml of DMF, are added 73.2 mg (0.6 mmol) of phenylboronic acid, 0.27 ml (0.3 mmol) of a 1.1M solution of sodium carbonate in water and 34.7 mg (0.03 mmol) of tetrakis(triphenylphosphine)palladium. The reaction medium is stirred for 17 hours at 100° C. After cooling, the reaction medium is filtered and the resin is rinsed with DMF (3 ml), THF (3 ml), with a 0.05 M solution of sodium diethyldithiocarbamate trihydrate in THF/H$_2$O (5×3 ml), and then again with THF (5×3 ml) and with dichloromethane (6×3 ml). After drying under vacuum, 205 mg of resin are obtained.

c) (4-Fluorobiphenyl-2-yl)acetic acid

A suspension of 196.1 mg (0.15 mmol) of the resin prepared in Example 25b in 5 ml of a 20% solution of trifluoroacetic acid in dichloromethane is stirred for 1 hour at room temperature. After filtering the reaction medium, the resin is rinsed with dichloromethane (3×5 ml).

The filtrate is concentrated under vacuum to give 39 mg of a cream-white solid.

Yield: quantitative.

LC-MS: (ES−): 229.1 (M-1).

EXAMPLES 26 TO 45

The compounds of Table 2 were obtained by working as in Example 25.

TABLE 2

| Ex | R2 | X | Y | R3 | NMR | LCMS |
|----|-----|----|----|--------|-----|------|
| 26 | F | CH | CH | 4-Me— | | (ES−): 243.2 |
| 27 | F | CH | CH | 4-F— | | (ES−): 247.2 |
| 28 | F | CH | CH | 4-MeO— | | (ES−): 259.2 |
| 29 | F | CH | CH | 4-F3C— | | (ES−): 297.2 |
| 30 | F | CH | CH | 4-MeSO2- | | (ES−): 307.1 |
| 31 | F | CH | CH | 4-Cl— | | (ES−): 263.1 |
| 32 | F | CH | CH | 4-Me2N— | (DMSO-D6) 2.9 (d, J = 5.1 Hz, 6 H); 3.5 (s, 2 H); 6.8 (m, 2 H); 7.1 (m, 5 H); 12.3 (s, 1 H) | |
| 33 | MeO | CH | CH | H | | (ES−): 241.2 |
| 34 | MeO | CH | CH | 4-Me— | | (ES−): 255.2 |
| 35 | MeO | CH | CH | 4-F— | | (ES−): 259.2 |
| 36 | MeO | CH | CH | 4-MeO— | | (ES−): 271.2 |
| 37 | MeO | CH | CH | 4-F3C— | | (ES−): 309.2 |
| 38 | MeO | CH | CH | 4-MeSO2- | | (ES−): 319.2 |
| 39 | MeO | CH | CH | 4-Me2N— | (DMSO-d6) 2.9 (s, 6 H); 3.5 (s, 2 H); 3.8 (s, 3 H); 6.7 (d, J = 8.7 Hz, 2 H); H); 6.9 (m, 2 H); 7.1 (m, 3 H) | (ES+): 286.2 |
| 40 | F | N | CH | H | | (ES+): 232.2 |
| 41 | F | CH | N | H | | (ES+): 232.2 |
| 42 | NO2 | CH | CH | 4-Me— | | (ES−): 270.3 |
| 43 | NO2 | CH | CH | 4-MeO— | | (ES−): 286.3 |
| 44 | NO2 | CH | CH | 4-Cl— | | (ES−): 290.2/ 292.1 1 chlorine atom |
| 45 | NO2 | CH | CH | 4-F3C— | (DMSO-D6) 3.7 (s, 2 H); 7.6 (dd, J = 8.3, 3.0 Hz, 3 H); 7.9 (d, J = 8.0 Hz, 2 H); 8.2 (dd, J = 8.4, 2.5 Hz, 1 H); 8.3 (d, J = 2.3 Hz, 1 H); 12.5 (s, 1 H) | |

EXAMPLE 46

[4-(Acetylamino)-4'-methoxybiphenyl-2-yl]acetic acid a) Ethyl (2-bromo-5-nitrophenyl)acetate A mixture composed of 5.21 g (20 mmol) of (2-bromo-5-nitrophenyl)acetic acid (*Zhumal Organicheskoi Khimii* (1974) 10, 92-5), 80 ml of absolute ethanol and 0.1 ml of concentrated sulfuric acid is refluxed for 6 hours. After cooling, the reaction medium is concentrated under vacuum and taken up in ether. This organic phase is washed with saturated $NaHCO_3$ solution and then with water, after which it is dried over $Na_2SO_4$. After concentrating under vacuum, 5.54 g of a beige solid are obtained.

Yield: 96.1%

NMR ($CDCl_3$): 1.3 (m, 3H); 3.9 (s, 2H); 4.2 (m, 2H); 7.8 (d, J=8.7 Hz, 1H); 8.0 (dd, J=8.7, 2.7 Hz, 1H); 8.2 (d, J=2.7 Hz, 1H).

b) Ethyl (4'-methoxy-4-nitrobiphenyl-2-yl)acetate

To a mixture of 576.2 mg (2 mmol) of the compound prepared in Example 46a, 115.6 mg (0.1 mmol) of tetrakis(triphenylphosphine)palladium, 254.4 mg (2.4 mmol) of caesium carbonate and 7.4 ml of toluene deoxygenated with a stream of nitrogen, are added 379.9 mg (2.5 mmol) of 4-methoxyphenylboronic acid, followed by addition of 4.42 ml of absolute ethanol. The reaction medium is heated at 90° C. for 16 hours. After cooling, 10 ml of water and 10 ml of ethyl acetate are added to the reaction medium, which is then filtered.

After separating out the organic phase by settling, the aqueous phase is re-extracted with ethyl acetate. The combined organic fractions are washed with water, dried over $NaSO_4$ and concentrated under vacuum. The residue obtained is purified by flash chromatography on a column of silica, with a dichloromethane/heptane mixture (3:1), to give 403 mg of an orange-coloured oil.

Yield: 63.9%

NMR ($CDCl_3$): 1.2 (t, J=7.1 Hz, 3H); 3.7 (s, 2H); 3.9 (s, 3H); 4.1 (q, J=7.1 Hz, 2H); 7.0 (m, 2H); 7.2 (m, 2H); 7.4 (d, J=8.4 Hz, 1H); 8.2 (dd, J=8.4; 2.4 Hz, 1H); 8.2 (d, J=2.4 Hz, 1H).

c) Ethyl (4-amino-4'-methoxybiphenyl-2-yl)acetate

A mixture of 345 mg (1.1 mmol) of the compound prepared in Example 46b, 200 mg of 10% Pd/C and 5 ml of absolute ethanol is hydrogenated at atmospheric pressure, at room temperature.

The Pd/C is then filtered off and rinsed with ethanol.

The filtrate is concentrated under vacuum to give 274 mg of a beige-coloured solid.

Yield: 87.8%

NMR (DMSO-$d_6$): 1.1 (t, J=7.1 Hz, 3H); 3.4 (s, 2H); 3.8 (s, 3H); 4.0 (q, J=7.1 Hz, 2H); 5.5 (s, 2H); 6.6 (m, 2H); 6.9 (m, 3H); 7.1 (m, 2H).

d) Ethyl [4-(acetylamino)-4'-methoxybiphenyl-2-yl]acetate

To a mixture of 142.7 mg (0.5 mmol) of the compound prepared in Example 46c, 0.139 ml (1 mmol) of triethylamine and 8 ml de dichloromethane are added, at 15° C., 39 µl (0.55 mmol) of acetyl chloride.

After stirring overnight at room temperature, the reaction medium is poured into water and extracted with dichloromethane. The combined organic phases are washed with water, dried over $Na_2SO_4$ and then concentrated under vacuum. The residue obtained is purified by flash chromatography on a column of silica, with a dichloromethane/ethyl acetate mixture (9:1), to give 142 mg of oil.

Yield: 86.7%

NMR ($CDCl_3$): 1.2 (t, J=7.2 Hz, 3H); 2.2 (s, 3H); 3.6 (s, 2H); 3.8 (s, 3H); 4.1 (q, J=7.2 Hz, 2H); 6.9 (d, J=8.6 Hz, 2H); 7.2 (m, 4H); 7.5 (m, 2H).

e) [4-(Acetylamino)-4'-methoxybiphenyl-2-yl]acetic acid

Obtained from the compound prepared in Example 46d by working as in Example 1b.

Yield: 57.4%

NMR (DMSO-$d_6$): 2.0 (m, 3H); 3.5 (s, 2H); 3.8 (m, 3H); 7.0 (m, 2H); 7.1 (dd, J=8.2 Hz, 2.7 Hz, 1H); 7.2 (m, 2H); 7.5 (m, 2H); 10.0 (s, 1H); 12.3 (s, 1H).

EXAMPLES 47 TO 50

The compounds of Table 3 were obtained by working as in Example 46.

TABLE 3

| Ex | R3 | NMR | LCMS |
|---|---|---|---|
| 47 | Cl | | (ES−): 302.3/304.3 1 chlorine atom |
| 48 | H | | (ES+): 270.3 |
| 49 | CF3 | (DMSO-D6) 2.1 (s, 3 H); 3.5 (s, 2 H); 7.2 (d, J = 8.2 Hz, 1 H); 7.6 (m, 4 H); 7.8 (d, J = 8.2 Hz, 2H); 10.1 (s, 1 H); 12.4 (s, 1 H) | (ES−): 336.3 |
| 50 | Me | (DMSO-D6) 2.1 (m, 3 H); 2.3 (s, 3 H); 3.4 (s, 2 H); 7.2 (m, 5 H); 7.5 (m, 2 H); 10.0 (s, 1 H); 12.3 (s, 1 H) | (ES−): 282.3 |

EXAMPLE 51

2-(4-Chlorobiphenyl-2-yl)ethanol a) Ethyl (4-chlorobiphenyl-2-yl)acetate

A mixture composed of 900 mg (3.65 mmol) of (4-chlorobiphenyl-2-yl)acetic acid (J. Am. Chem. Soc. (1955), 77, 2325), 25 ml of absolute ethanol and 50 µl of concentrated sulfuric acid is refluxed for 8 hours. After cooling and concentrating under vacuum, the reaction medium is taken up in ether, washed with saturated $NaHCO_3$ solution and then with water, and then dried over $Na_2SO_4$. After concentrating under vacuum, 1 g of a yellow oil is obtained.

Yield: quantitative

NMR ($CDCl_3$): 1.1 (t, J=7.1 Hz, 3H); 3.5 (s, 2H); 4.0 (q, J=7.1 Hz, 2H); 7.1 (d, J=8.2 Hz, 1H); 7.2 (m, 3H); 7.3 (m, 4H).

b) 2-(4-Chlorobiphenyl-2-yl)ethanol

Under a nitrogen atmosphere, 414.4 mg (10.9 mmol) of $LiAlH_4$ pellets are crumbled in 30 ml of THF, followed by dropwise addition over 15 minutes of 1 g (3.64 mmol) of the compound prepared in Example 51a, dissolved in 15 ml of THF.

The reaction medium is heated at 60° C. 43 hours. After cooling, the mixture is hydrolysed by addition of water, followed by addition of 35 ml of ethyl ether and then 10 g of sodium sulfate. After filtering and concentrating the field rate under vacuum, a pale yellow oil is obtained, which is purified by flash chromatography on a column of silica in dichloromethane to give 791 mg of a yellow oil.

Yield: 93.4%

NMR ($CDCl_3$): 1.3 (s, 1H); 2.8 (t, J=6.9 Hz, 2H); 3.7 (t, J=6.8 Hz, 2H); 7.2 (d, J=8.2 Hz, 1H); 7.3 (m, 3H); 7.4 (m, 4H).

EXAMPLE 52

2-(4'-Chlorobiphenyl-2-yl)ethanol a) Ethyl (4'-chlorobiphenyl-2-yl)acetate

Prepared from (4'-chlorobiphenyl-2-yl)acetic acid (*J. Am. Chem. Soc.* (1955), 77, 2325) by working as in Example 51a.
Yield: quantitative
NMR (CDCl$_3$): 1.1 (t, J=7.1 Hz, 3H); 3.5 (s, 2H); 4.0 (q, J=7.1 Hz, 2H); 7.2 (m, 8H).

b) 2-(4'-Chlorobiphenyl-2-yl)ethanol

Obtained by working as in Example 51b.
Yield: 92.1%
NMR (CDCl$_3$): 1.2 (s, 1H); 2.8 (t, J=6.9 Hz, 2H); 3.6 (t, J=7.0 Hz, 2H); 7.2 (m, 8H).

EXAMPLE 53

3-(4-Chlorobiphenyl-2-yl)propanenitrile a) 2-(2-Bromoethyl)-4-chlorobiphenyl

To a solution, maintained at 5° C., of 710 mg (3.05 mmol) of 2-(4-chlorobiphenyl-2-yl)ethanol, prepared in Example 51, in 10 ml of toluene are added 97 µl (1.02 mmol) of PBr$_3$, and the reaction medium is allowed to return to room temperature. After stirring for 20 hours, the reaction medium is poured into 100 ml of water and extracted with ethyl acetate. The organic phase is washed with water, dried over Na$_2$SO$_4$ and then concentrated under vacuum to give a yellow liquid, which is purified by flash chromatography on a column of silica, in dichloromethane. 360 mg of a pale yellow oil are obtained.
Yield: 39.9%
NMR (CDCl$_3$): 3.1 (t, J=7.6 Hz, 2H); 3.3 (t, J=7.6 Hz, 2H); 7.1 (d, J=8.0 Hz, 1H); 7.2 (m, 4H); 7.3 (m, 3H).

b) 3-(4-Chlorobiphenyl-2-yl)propanenitrile

A mixture of 350 mg (1.18 mmol) of the compound prepared in Example 53a, 98.7 mg (2.01 mmol) of NaCN and 3 ml of DMF dried over molecular sieves is heated at 80° C. for four hours, and then poured into 40 ml of water and extracted with ethyl ether (2×50 ml). The organic phase is washed with 0.5N sodium hydroxide solution and then with water and dried over Na$_2$SO$_4$, after which it is concentrated under vacuum to give 286 mg of a pale yellow liquid.
Yield: quantitative
IR: ν=2247 cm$^{-1}$ (CN)
NMR (CDCl$_3$): 2.4 (t, J=7.6 Hz, 2H); 2.9 (t, J=7.5 Hz, 2H); 7.2 (m, 5H); 7.4 (m, 3H).

EXAMPLE 54

3-(4-Chlorobiphenyl-2-yl)propanoic acid

A mixture composed of 280 mg (1.16 mmol) of 3-(4-chlorobiphenyl-2-yl)propanenitrile prepared in Example 53, 138 mg (3.475 mmol) of NaOH, 4 ml of ethanol and 4 ml water is refluxed for 6 hours. After cooling, the ethanol is concentrated under vacuum. 16 ml of water are then added and the mixture is washed with ethyl ether (2×20 ml), followed by acidification of the aqueous phase with 16% HCl. The resulting mixture is extracted with dichloromethane and the extracts are then dried over sodium sulfate. After concentrating the organic phase under vacuum, an oil is obtained, which crystallises after stirring in pentane, to give 171 mg of a white solid.
Yield: 56.6%
NMR (DMSO-d$_6$): 2.4 (t, 2H); 2.8 (t, J=7.9 Hz, 2H); 7.4 (m, 8H), 12.1 (s, 1H).
LC-MS: (ES$^-$)=259.1/261.1; 1 chlorine atom.

Biochemical Test

Objective

Demonstration of Inhibition of the Activity of the Chosen Caspase by a Delayed-Time Fluorescence Method.

Principle of the Method

Caspases are cysteine proteases that have a strict specificity of cleavage of their substrate after an aspartic acid residue.

The substrate used is a tetrapeptide specific to this caspase, having at one of its ends a fluorescent europium marker (W1284) and at the other end a europium chelate fluorescence quencher (QSy-7): Eu-W1284-CIETDK-QSy-7. The europium chelate (W1284) and the fluorescence quencher (QSy-7) are protected molecules and the property of Wallac Oy, a division of Perkin Elmer.

The caspase cleaves the substrate, releasing the quencher. Thus, by excitation at 340 nm, the signal emitted by the fluorescence of the europium is read by WALLAC Victor$^2$ reader at 615 nm.

A product capable of inhibiting the activity of this enzyme will be detected by inhibition of the fluorescence relative to the fluorescence detected in the sample incubated without inhibitors (100%).

Procedure

Reagents
  The caspase reaction buffer: the Pipes (piperazine-N,N'-bis[2-ethanesulfonic acid]), sucrose, EDTA-Na2 (disodium salt of ethylenediaminetetraacetic acid), CHAPS (3-[(3-cholamidopropyl)dimethylammonio]-1-propanesulfonate) and DTT (dithiothreitol) are obtained from Sigma, the sodium hydroxide (NaOH) as a 1N solution, NaCl and DMSO are of analytical grade and are obtained from Merck, and the distilled water is obtained from BDH Laboratories.
The caspase substrates: the substrate for caspases 2 and 3 is Eu-W1284-CDEVDK-QSy-7, the substrate for caspase 6 is Eu-W1284-CVEIDK-QSy-7, the substrate for caspases 8 and 10 is Eu-W1284-CIETDK-QSy-7 and the substrate for caspase 9 is Eu-W1284-CLEHDK-QSy-7, and they are all obtained from Wallac Oy, a division de Perkin Elmer.
Recombinant human caspases: caspases 2, 3, 6 and 10 are obtained from Biomol, except for caspase 8 and caspase 9, which are obtained from Calbiochem, a division of Merck Biosciences.
The standard caspase inhibitors: The irreversible inhibitor chosen as standard for caspase 2 is z-(benzyloxycarbonyl)-D(OMe)VAD(OMe)-fmk (fluoromethyl ketone), z-D(OMe)E(OMe)VD(OMe)-fmk for caspase 3, z-VE(OMe)ID(OMe)-fmk for caspase 6, z-IE(OMe)TD(OMe)-fmk for caspase 8 and caspase-10 and z-LE(OMe)HD(OMe)-fmk for caspase 9. All the inhibitors are obtained from Calbiochem, a division of Merck Biosciences.
The specific caspase-10 inhibitors are obtained from chemical synthesis on the base of the formula I and are supplied in powder form.

Preparation

The caspase buffer (Stennicke and Salvesen, J. Biol. Chem. 272 (1997) 25719-25723): 20 mM Pipes, 100 mM NaCl, 10 mM DTT, 0.1% CHAPS, 10% sucrose, 1 mM EDTA, pH 7.2. The buffer is prepared in 9/10 of the final volume and stored at 4° C., followed by addition of 1/10 of the volume of DTT (100 mM) extemporaneously on the day of the assay.

The substrates: Stored at −80° C. and thawed on ice for 5-10 min. After pelletising the powder, the flask is opened and the contents are taken up in 0.4 ml of distilled $H_2O$ to obtain a final concentration of 10 μM. Dissolution is continued for 15 minutes on ice, and the substrate is then ready for use or can be divided into aliquots and stored at −80° C. The substrate is diluted 25× in the caspase buffer (400 nM) and then deposited (10 μl) in the assay well at a final concentration of 120 nM (dilution 1/3.3).

The caspases: All the caspases, except for caspase 9, which is freeze-dried, are supplied in solution form (50 U/μl). They are ready for use or can be divided into aliquots and stored at −80° C. The assay is performed with 25 U of caspase per well, the volume of enzyme (50 U/μl) adapted to the number of wells is taken up and diluted 40× in the caspase buffer (1.25 U/μl). 20 μl of this solution are distributed per well of the assay plate. For caspase 9, the lyophilisate is reconstituted in PBS (1 U/μl) and diluted 20× in the caspase buffer (0.05 U/μl). The assay is performed with 1 U of enzyme per well, by distributing 20 μl of the diluted solution per well.

The standard inhibitors: The standard inhibitors are dissolved in DMSO to a concentration of 10 mM. They are tested at $IC_{20}$ and at $IC_{50}$ on the caspases they inhibit (see following table). The concentrations mentioned in the table are the final concentrations in the assay wells.

|  | $IC_{50}$ | $IC_{20}$ |
|---|---|---|
| z- DVAD - fmk | 450 nM | 3 μM |
| z- DEVD - fmk | 600 nM | 1.5 μM |
| z- VEID - fmk | 1 μM | 3 μM |
| z- LEHD - fmk | 40 nM | 200 nM |
| z- IETD - fmk (caspase 8) | 800 nM | 1.5 μM |
| z- IETD - fmk (caspase-10) | 15 nM | 80 nM |

The standards for $IC_{20}$ and $IC_{50}$ are diluted to intermediate concentrations in DMSO (for example: 23.5 μM for z-IETD-fmk at 80 nM for caspase-10 and 4.41 μM for 15 nM) and all prediluted (1/26.67) in the caspase buffer (1.5 μl in 40 μl (final volume) of caspase buffer). They are then distributed in the wells using this solution to reach the final concentration of $IC_{20}$ or $IC_{50}$, i.e. 3 μl in 33 μl of final reaction volume (dilution 1/11). Thus, the final concentration of DMSO in the well is 0.3% (v/v) final. The factor z as described in Zhang et al. J. Biomol. Screen. 4 (1999) 67-73 is always greater than 0.5 for all the standard inhibitors listed in the above table, tested at $IC_{50}$ and compared with the respective control without inhibition (100%).

The specific caspase-10 inhibitors: The synthetic products are dissolved in DMSO to a concentration of 20 mM. An intermediate dilution (1/6.6) is pre-pared in DMSO by diluting 10 μl of the concentrated solution in 66 μl of DMSO (final volume). They are then prediluted (1/26.67) in the caspase buffer, as for the standards, by diluting 1.5 μl of this solution in 40 μl of buffer (final volume). The inhibitors are then distributed in the wells to reach the final screening concentration (10 μM), i.e. 3 μl in 33 μl of final reaction volume (dilution 1/11) and a final concentration of DMSO of 0.3% (v/v) in the well.

Protocol:

The assay is performed in black 384- or 96-well microassay plates (COSTAR) with an untreated surface. The volumes and the protocol were optimised for automated use.

| TEST (total volume = 33 μl) | BLANK (total volume = 33 μl) |
|---|---|
| 20 μl buffer with enzyme | 20 μl buffer |
| 3 μl inhibitor or standard/DMSO predicted | 3 μl DMSO prediluted |
| 10 μl substrate | 10 μl substrate |

The incubation takes place for 3 hours 30 minutes at room temperature before reading the fluorescence in delayed time on the WALLAC Victor$^2$ reader with the filters corresponding to the fluorescence of europium (excitation filter: 340 nm, emission filter: 615 nm).

The inhibitors which have a signal ≦60% of the control without inhibitor (100%) and which are specific for caspase-10, i.e. which do not inhibit (≧60% of the control) the other caspases, are selected for the determination of the $IC_{50}$ on caspase-10 and the other caspases.

Determination of the $IC_{50}$ on caspase-10 and the other caspases: specificity of inhibition: Same protocol as described previously, the inhibitors selected for their specificity of inhibition of caspase-10 at 10 μm are then tested from 100 nM to 200 μM on caspase-10 and also on the other caspases (2, 3, 6, 8 and 9). The inhibitors are diluted using solutions with concentrations of less than 20 mM in DMSO, and then prediluted in the caspase buffer. These predilutions are prepared by diluting 5 μl of the stock solution in 40 μl of caspase buffer (final volume) and the various points of the concentration range (0.123; 0.37; 1.11, 3.3; 10; 25; 50; 75; 100 and 200 μM) are reached in the well by distributing 3 μl of these solutions in 33 μl of final volume (dilution 1/11). Similarly, the standard caspase-10 inhibitor at $IC_{50}$ and at $IC_{20}$ are prediluted by diluting 5 μl of the stock solution (7.9 μM in DMSO for $IC_{50}$, 80 nM) in 40 μl of caspase buffer. For the $IC_{50}$ values, the final DMSO concentration in the wells is 1% instead of 0.3% in the screening protocol. For the specific caspase-10 inhibitors, the $IC_{50}$ values are thus determined on all the caspases. The specificity factor for caspase-10 is calculated as the following ratio:

Specificity factor=ratio [$IC_{50}$ caspase x/$IC_{50}$ caspase-10]

with x=2, 3, 6, 8 or 9

The results are summarised in the following table:

| | Inhibition ($IC_{50}$ μM) | | | | | |
|---|---|---|---|---|---|---|
| Ex | Caspase-2 | Caspase-3 | Caspase-6 | Caspase-8 | Caspase-9 | Caspase-10 |
| 12 | >200 | >200 | >200 | >200 | >200 | 13.1 |
| 14 | >200 | >200 | >200 | >200 | >200 | 10.1 |
| 15 | >200 | >200 | >200 | >200 | >200 | 23.6 |
| 16 | >200 | >200 | >200 | >200 | >200 | 9.0 |

The invention claimed is:

1. A compound of formula (II):

in which:
X, Y and Z, which may be identical or different, each independently represent a —CH═ group or a nitrogen atom wherein if one of X, Y or Z is nitrogen the other two are —CH═;
m is an integer 1, 2, 3, 4 or 5;
R1 represents —COOR, —CH$_2$CN, or —CH$_2$OH,
in which
R represents a hydrogen atom, -alkyl optionally substituted by a halogen atom, —OH, —CN, —Oalkyl, -Aryl, —OR', —NO$_2$, —NRR', -alkylaryl or -perhaloalkyl,
or R represents an -aryl, -alkylaryl or -heteroaryl group, each optionally substituted by a halogen atom, —OR, —CN, -Aryl, NO$_2$, —NRR', -alkylaryl or -perhaloalkyl;
in which R' represents an -alkyl group optionally substituted by a halogen atom, —OR, —CN, —COOR, —NRR', —NO$_2$, -aryl, -alkylaryl or perhaloalkyl;
R2 represents a halogen atom, —NO$_2$, —NRCOR', optionally perhalogenated -alkyl, —OH, —CN, —COOR, -alkylaryl, or an alkyl group substituted by a halogen atom —OR, —CN, —NRR', —COOR, —NO$_2$, -aryl, -alkylaryl or perhaloalkyl;
each of the R3, which may be identical or different, independently represents a halogen atom, optionally perhalogenated -alkyl, optionally perhalogenated —Oalkyl, —S(O)$_p$alkyl, —NRR', —OR, —CN, —NO$_2$,
-aryl, -alkylaryl, or an -alkyl group, each optionally substituted by a halogen atom, —OR, —CN, —NRR', —NO$_2$, -aryl, -alkylaryl or perhaloalkyl;
in which p=0, 1 or 2 and one R3 is in the para position relative to the phenyl ring;
or tautomeric forms, enantiomers, diastereoisomers, epimers, or pharmaceutically acceptable salts thereof,
with the exception of compounds of formula (II) for which:
if X═Y═C,
R2═-Cl,
R1═—CO$_2$H, m=2 and R3=(2-Cl, 6-Cl).

2. A compound according to claim 1, which is:
[4-chloro-4'-(methylsulfonyl)biphenyl-2-yl]acetic acid
[4-chloro-4'-(dimethylamino)biphenyl-2-yl]acetic acid
(4-chloro-4'-methylbiphenyl-2-yl)acetic acid
(4-chloro-4'-fluorobiphenyl-2-yl)acetic acid
(4,4'-dichlorobiphenyl-2-yl)acetic acid
[4-chloro-4'-(trifluoromethyl)biphenyl-2-yl]acetic acid
(4-chloro-4'-methoxybiphenyl-2-yl)acetic acid
(4'-tert-butyl-4-chlorobiphenyl-2-yl)acetic acid
[4-chloro-4'-(trifluoromethoxy)biphenyl-2-yl]acetic acid
[4,4'-bis(trifluoromethyl)biphenyl-2-yl]acetic acid
(4-fluoro-4'-methylbiphenyl-2-yl)acetic acid
(4,4'-difluorobiphenyl-2-yl)acetic acid
(4-fluoro-4'-methoxybiphenyl-2-yl)acetic acid
[4-fluoro-4'-(trifluoromethyl)biphenyl-2-yl]acetic acid
[4-fluoro-4'-(methylsulfonyl)biphenyl-2-yl]acetic acid
(4'-chloro-4-fluorobiphenyl-2-yl)acetic acid
[4'-(dimethylamino)-4-fluorobiphenyl-2-yl]acetic acid
(4'-methyl-4-nitrobiphenyl-2-yl)acetic acid
(4'-methoxy-4-nitrobiphenyl-2-yl)acetic acid
(4'-chloro-4-nitrobiphenyl-2-yl)acetic acid
[4-nitro-4'-(trifluoromethyl)biphenyl-2-yl]acetic acid
[4-(acetylamino)-4'-methoxybiphenyl-2-yl]acetic acid
[4-(acetylamino)-4'-chlorobiphenyl-2-yl]acetic acid
[4-(acetylamino)-4'-(trifluoromethyl)biphenyl-2-yl]acetic acid
[4-(acetylamino)-4'-methylbiphenyl-2-yl]acetic acid
or tautomeric forms, enantiomers, diastereoisomers, epimers, or pharmaceutically acceptable salts thereof.

3. A compound according to claim 1, which is:
(4-chloro-4'-methylbiphenyl-2-yl)acetic acid
(4,4'-dichlorobiphenyl-2-yl)acetic acid
[4-chloro-4'-(trifluoromethyl)biphenyl-2-yl]acetic acid
(4-chloro-4'-methoxybiphenyl-2-yl)acetic acid
or tautomeric forms, enantiomers, diastereoisomers, epimers, or pharmaceutically acceptable salts thereof.

4. A pharmaceutical composition comprising a compound of formula (II) as defined according to claim 1 and a pharmaceutically acceptable excipient.

* * * * *